United States Patent [19]

Sandrik et al.

[11] Patent Number: 5,236,363

[45] Date of Patent: Aug. 17, 1993

[54] PHANTOM FOR SIMULATING AN X-RAY EXAM PATIENT

[75] Inventors: John M. Sandrik, Wauwatosa; Gordon M. Geiger, Waukesha, both of Wis.

[73] Assignee: General Electric Company, Milwaukee, Wis.

[21] Appl. No.: 743,465

[22] Filed: Aug. 9, 1991

[51] Int. Cl.$^5$ ............................................. G01D 14/00
[52] U.S. Cl. ........................................ 434/267; 378/18
[58] Field of Search ............. 378/18, 207; 128/653.5; 250/252.1, 327.2; 434/267, 272, 274

[56] References Cited

U.S. PATENT DOCUMENTS

| | | |
|---|---|---|
| 4,126,789 | 11/1978 | Vogl et al. |
| 4,472,829 | 9/1984 | Riederer et al. |
| 4,649,561 | 3/1987 | Arnold ............................. 250/252.1 |
| 4,788,706 | 11/1988 | Jacobson |
| 5,049,748 | 9/1991 | Ito et al. |
| 5,071,602 | 12/1991 | Nambu et al. ............. 128/653.5 X |

FOREIGN PATENT DOCUMENTS

| | | |
|---|---|---|
| 377690 | 4/1985 | Austria |
| 0082733 | 6/1983 | European Pat. Off. |
| 8807358 | 7/1988 | Fed. Rep. of Germany |

OTHER PUBLICATIONS

"Radiology Instruments and Accessories" Nuclear Associates Catalog G-4, pp. 14, 36, 37, 42, 43, 58, 59, 62 and 63 (1985).

"Quality Assurance in Radiology Product Catalog," Radiation Measurement, Inc. Catalog, pp. 13, 15, 26, 27 and 29 (1989).

"Cardiovascular Phantom", General Electric Medical Systems Division, Direction 14409A, 1979.

Leibovic, S. J. et al. "Reducing Patient Dose in Voiding Cystourethrogaphy," Urol. Radiol. 2, 103–107 (1980).

Darling, d. B., "Voiding Cystourethrography" *Radiography of Infants and Children*, pp. 154–165 (1979) Charles C. Thomas, Publisher.

Merrill, V., "Urinary System" in *Atlas of Reoentgenographic Positions and Standard Radiologic Procedures*, vol. 3, pp. 764–769 (1975) C. V. Mosby Company, Publishers.

Clark, K. C., "Urinary Tract, Urography Cystography" *Positioning in Radiography*, pp. 564–565 (1964), Heinemann Medical Books Ltd., Publishers. "Advantx Radiography and Fluoroscopy Systems", GE Medical Systems (1990).

*Primary Examiner*—Richard J. Apley
*Assistant Examiner*—Glenn E. Richman
*Attorney, Agent, or Firm*—Quarles & Brady

[57] ABSTRACT

A phantom for simulating a patient during an X-ray exam that involves introducing a high contrast material into the patient. The phantom comprises a base and a first contrast element. The first contrast element is disposed within the base and has an X-ray attenuation greater than that of the base. The contrast ratio of the first contrast element to the base is approximately 50. In one embodiment of the phantom, the first contrast element contains iodine. In another embodiment, the base has a shape which occupies the entire field of view of the X-ray exam and the first contrast element is positioned substantially in the center of the field of view. In yet another embodiment of the phantom, a second contrast element is disposed within the base and has a contrast ratio to the base of approximately 1.5.

11 Claims, 2 Drawing Sheets

PHANTOM FOR SIMULATING AN X-RAY EXAM PATIENT

BACKGROUND OF THE INVENTION

1. Field of the Invention

The field of the invention is phantoms used to simulate the human body during a radiologic examination. In particular, the field of the invention is phantoms used to simulate radiologic imaging during an X-ray examination in which a high contrast substance is introduced into the patient.

2. Background Art

X-rays are short wavelength electromagnetic waves of $10^{-3}$ to 10 nm. These waves can be produced when high speed electrons strike a solid target. Because X-rays penetrate materials that are opaque to light, such as the human body, and may be detected photographically, they are of great use in medical diagnostics. In a typical X-ray examination, the patient is positioned between the X-ray emitting device and a piece of X-ray-sensitive film. As the X-rays encounter internal organs and bones, they will be absorbed, scattered, or transmitted. The transmitted X-rays can register an image on the film. In this manner, an image of the patient's internal organs can be obtained.

In more advanced X-ray examination systems, the image obtained from the X-ray bombardment is translated into a fluorographic image that may be viewed on a TV screen. This image translation is an advantage during a prolonged exam when many images must be viewed or when the purpose of the exam is to visualize the organs working together. We call this image translation the "image acquisition system."

X-ray phantoms are devices used to simulate the human body during an X-ray examination. A phantom is usually composed of material that mimics human tissue in its ability to produce absorption and scattering of radiation. This ability to absorb and scatter radiation is expressed by the attenuation coefficient, which is a function of chemical elements of which the material is composed and the spectrum of energies used in the examination. Variations of attenuation coefficients and thicknesses among materials produce contrast in an X-ray image. Two substances with the same attenuation coefficient and thickness will similarly absorb and scatter X-rays under given imaging conditions and will produce the same contrast with respect to a third substance during an X-ray examination.

We define the "contrast ratio" of a contrast element as the quotient of the quantity of X-rays transmitted by a reference material to the quantity of X-rays transmitted by the contrast element for specified imaging conditions. When numerical values of contrast ratio are stated herein, they refer to the following imaging conditions:

(a) The X-ray emitting device provides a bremsstrahlung spectrum with a maximum energy of 80 keV and filtered by 0.2 mm copper in addition to the inherent filtration of the X-ray tube, housing, and collimator, (b) the ratio is calculated in terms of the quantity (mR/mAs) of primary (unscattered) radiation exiting the phantom; exposure due to scattered radiation is subtracted.

Simulations using an X-ray phantom can be useful in calibrating the dosage to be used during an X-ray procedure. X-ray phantoms are also useful in calibrating the image acquisition system that converts the X-ray image into a fluorographic image that may be visualized on a screen during the X-ray exam. By using a phantom, the X-ray technician obtains reproducible imaging conditions and avoids exposing a patient to unnecessary radiation.

One example of an exam in which a phantom would be useful is a voiding cystourethrogram (VCUG). In this diagnostic exam, a patient's bladder is filled with an iodine-containing compound. Because iodine has a very high attenuation coefficient, the contrast ratio of the iodine-filled bladder and urethra will be high with respect to the organs and tissues surrounding them. The bladder, the urethra and other elements of the urinary system will become visible to the diagnostician through a fluoroscopic image obtained from the original X-ray image. A VCUG is often performed on patients to diagnose abnormalities of the bladder and urethra. A VCUG exam is simply one example of an X-ray examination procedure in which a high contrast substance is introduced into the patient.

VCUG exams present specific radiologic imaging problems. Existing phantoms fail to simulate the high contrast between the patient's iodine-filled bladder and the patient's soft tissues and bones. This failure is especially troublesome with pediatric patients who have a small body mass and less dense bones. In these pediatric patients, the contrasts between the iodine-filled bladder and these low attenuation value elements is overwhelming.

An additional problem with existing phantoms used in VCUG exams concerns the failure of the phantom to mimic the size and positioning of the patient's bladder in the X-ray field. This failure results in an over-exposed image for the following reason: During the VCUG exam, a large quantity of iodine-containing contrast medium is introduced into the patient's urinary bladder, and the patient's bladder is frequently positioned in the center of the X-ray image. In most X-ray examination mechanisms, a sensing window of the automatic exposure control (AEC) that controls the quantity of radiation used to acquire the image senses the radiation in the center of the X-ray image. Positioning the patient's bladder in the center of the X-ray screen places the bladder in the center of this sensing window. Since the iodine-containing bladder transmits very little X-radiation, the image in that region is very dark. If not calibrated to account for the low X-ray transmission in the bladder region, the AEC reacts by causing an overexposure of the portion of the image that surrounds the bladder.

What is needed in the art of X-ray phantoms is a phantom capable of simulating a patient during an X-ray examination that involves introducing a high contrast substance into the patient.

SUMMARY OF THE INVENTION

The present invention is a phantom for simulating a patient during an X-ray exam that involves introducing a high contrast substance into the patient. The phantom comprises a base and a first contrast element. The first contrast element is disposed within the base. The first contrast element has a greater X-ray attenuation than that of the base. The contrast ratio of the first contrast element and the base is approximately 50.

In a particularly advantageous embodiment, the contrast element contains iodine and is at the center of the phantom.

In another embodiment, the phantom contains a second contrast element meant to simulate a pediatric pelvic bone. The contrast ratio of the second contrast element to the base is approximately 1.5.

In another advantageous embodiment, the first contrast element is of a shape and size that mimics a child's bladder when filled with fluid.

The object of the present invention is to simulate a patient during an X-ray exam that involves introducing a high contrast substance into the patient. Another object of the invention is to simulate a VCUG patient.

It is an advantage of the present invention that the first contrast element effectively mimics the attenuation value of an iodine-filled bladder of a VCUG patient. The contrast ratio of the first contrast element to the base mimics the contrast ratio of the iodine-filled bladder to the soft tissue in a VCUG patient. Thus, the present invention allows an X-ray technician to calibrate an X-ray machine, either to determine dosage or to adjust an image acquisition system, without exposing a human patient to excess radiation.

Although existing phantoms fail to mimic the contrast between the soft tissues and iodine-filled bladder of any VCUG patient, this failure is more burdensome during a pediatric VCUG exam because the contrast of these elements is so great. It is an additional advantage of the present invention that the first contrast element and the base can be created to mimic the contrast between an iodine-filled pediatric bladder and pediatric soft tissues over a wide range of X-ray energies. Therefore, the contrast ratio of the first contrast element and the base mimics a pediatric VCUG patient and the phantom can be used to simulate a pediatric VCUG patient.

It is another advantage of the present invention that the first contrast element is at the center of the phantom, corresponding to where the image of the iodine-filled bladder of the VCUG patient would be in the X-ray screen. This placement allows the X-ray technician to correct for over-exposure due to the AEC system's reaction to the centrally placed high contrast element.

It is another advantage of the present embodiment that a second contrast element effectively mimics the contrast of a patient's pelvic bones and spine with respect to the soft tissues. The second contrast element can be created to specifically mimic the low density of pediatric bones.

The foregoing and other objects and advantages of the invention will appear from the following description. In the description, references are made to the accompanying drawings which form a part hereof and in which there is shown by way of illustration a preferred embodiment of the invention. Such embodiment does not necessarily represent the full scope of the invention, however, and reference must be made therefor to the claims herein for interpreting the scope of the invention.

DETAILED DESCRIPTION OF THE PREFERRED EMBODIMENT

Figure 1:
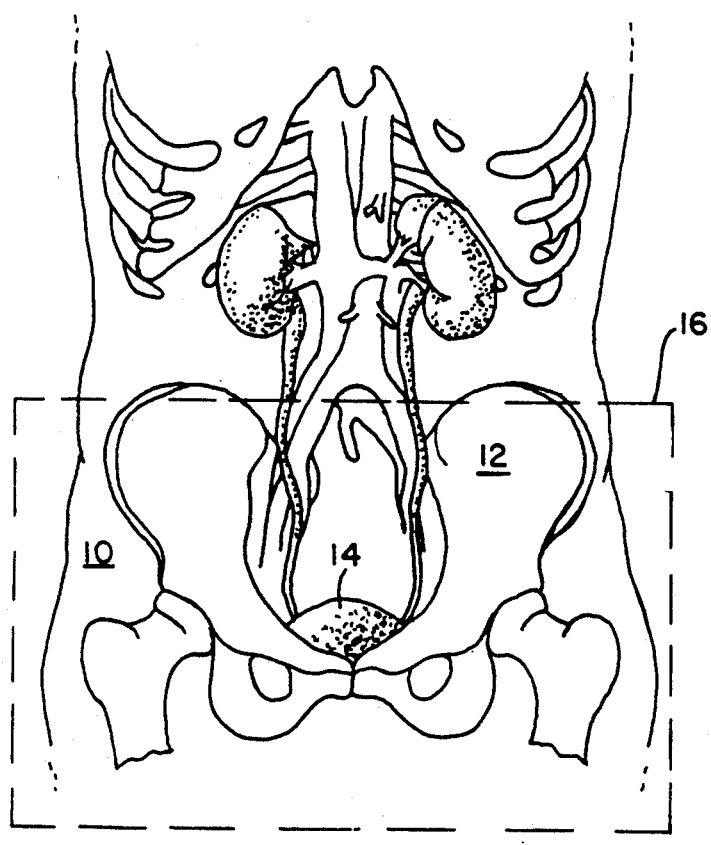
FIG. 1 is a cross-sectional view of a human patient.

FIG. 1 is a cross-sectional view of a male patient, featuring the urinary system. FIG. 1 represents an adult patient, but the spatial relationship between the urinary system, pelvic bones and soft tissue is similar in a pediatric patient. Basically, the present invention has components designed to mimic the X-ray attenuation of the patient's soft tissue 10 and the bones of the pelvis 12. The present invention also has a component designed to mimic the X-ray attenuation of the bladder 14 when it is filled with a high contrast liquid. The dashed lines 16 represent a typical X-ray field.

Figure 2:
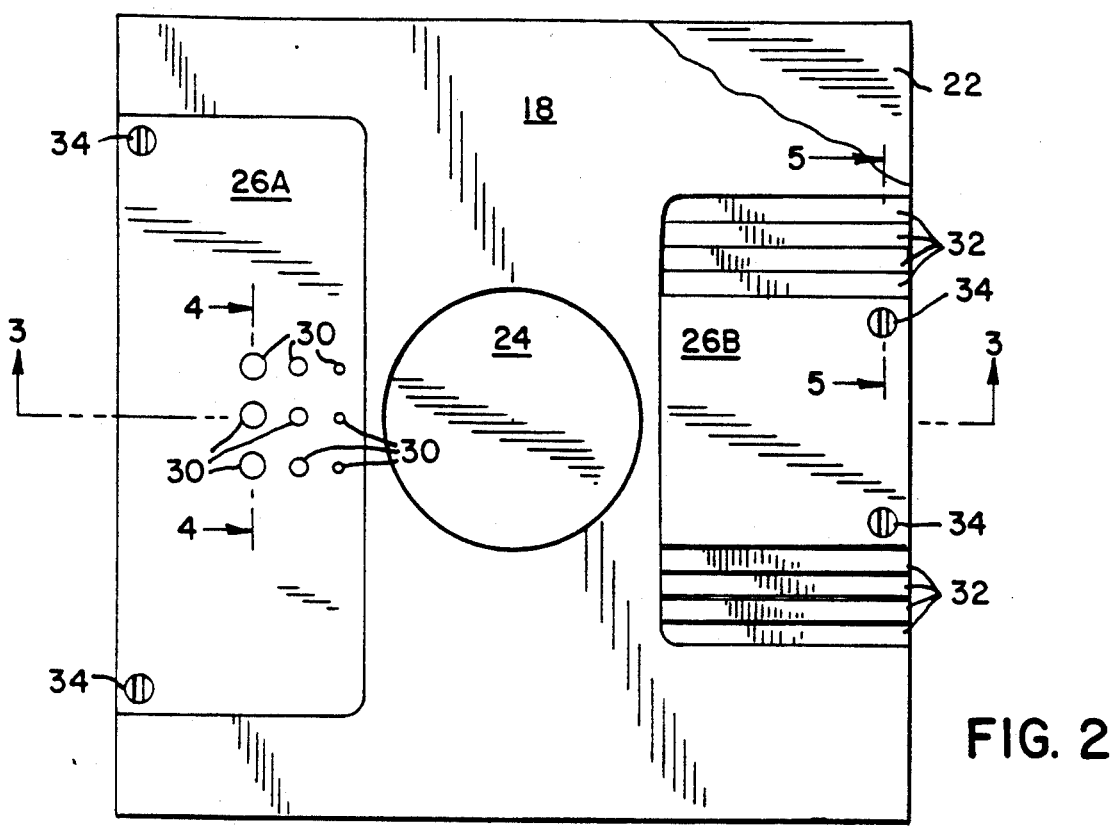
FIG. 2 is a top perspective view of a preferred embodiment of the present invention.
Figure 3:
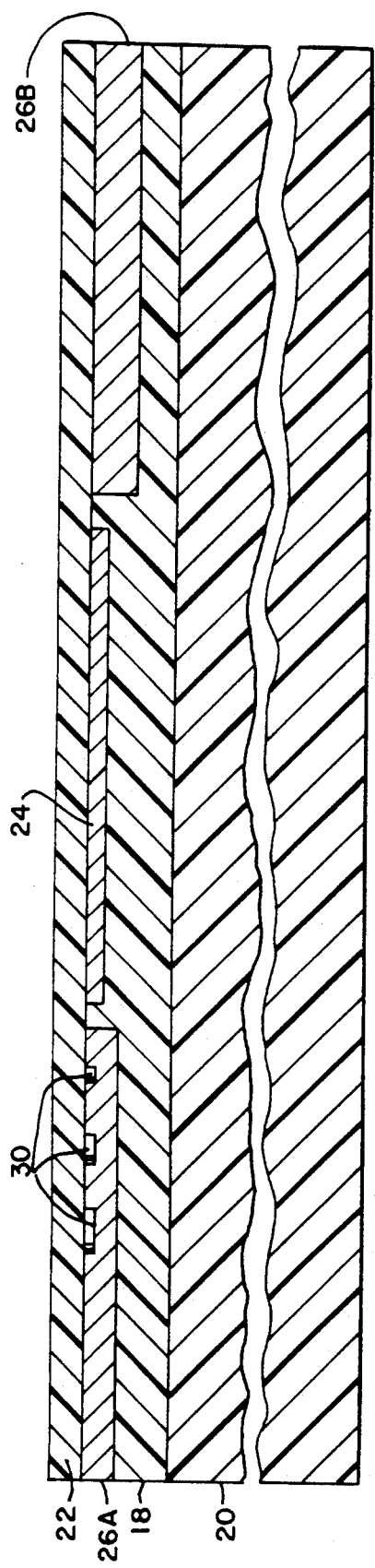
FIG. 3 is a cross-sectional view taken through line 3—3 in FIG. 2.

FIG. 2 is a top perspective view and FIG. 3 is a cross-sectional view of the preferred embodiment of the present invention. This phantom is meant to be positioned between an X-ray emission and an X-ray detection mechanism. In the preferred embodiment, the phantom simulates the X-ray attenuation of a pediatric patient during a VCUG exam. Therefore, the X-ray technician may determine a useful X-ray dose for a pediatric VCUG exam or calibrate an image acquisition system so that a useful image of a pediatric VCUG exam may be obtained.

Referring again to FIGS. 2 and 3, the phantom is a relatively thin rectangular structure comprised of a base layer 18 which is disposed between a support layer 20 and a cover layer 22. The base 18 is square and mimics the width of the pelvic area of a typical pediatric patient. The base 18 is stacked on the support 20 in the path of the X-rays and adds to the X-ray attenuation. The cover 22 is bonded to the top of the base 18. The cover 22 adds to the total X-ray attenuation as well as protecting the phantom components. The X-ray attenuation of the base 18, the support 20 and the cover 22 together mimic the X-ray attenuation of the pediatric patient's soft tissues 10. A particularly advantageous material for the support 20, the base 18 and the cover 22 is acrylic, and in the preferred embodiment, the thickness of the base 18 is 0.5 in, the thickness of the support 20 is 2.25 in and the thickness of the cover 22 is 0.125 in. The total thickness of acrylic in the base 18, support 20 and cover 22 is 2.88 in. This thickness mimics the X-ray attenuation of a small pediatric patient (2.75 in–3.5 in thick).

An acrylic block similar in shape to the support element 20 is a common part of a kit presently used by X-ray technicians to calibrate X-ray machines. By enabling the support 20 to be used in conjunction with the base element 18, an X-ray technician who wishes to calibrate an X-ray machine for a ACUG exam need only add the base 18 to his or her kit since the support 20 will already be a part of that kit. If this compatibility is not required, the support 20 and the base 18 may be formed as one element.

Referring again to FIG. 2, a first contrast element 24 is disposed within the base 18. In the preferred embodiment, the first contrast element 24 contains potassium iodide powder mixed with epoxy and formed into a circular plug. This plug is fitted into a similarly sized hole that has been milled into the base 18. The first contrast element 24 mimics the X-ray attenuation and size of an iodine-filled pediatric bladder. A suitable size for the first contrast element 24 is a disk with a diameter of 65 mm and a thickness of 6.28 mm. A suitable concentration of potassium iodide is 0.621 g/cm$^2$. This first contrast element 24 is comparable in size and shape to the bladder of a one to two year old child.

The first contrast element 24 contains a material having an X-ray attenuation greater than that of the base 18 plus support 20 plus cover 22 in order to effectively mimic the X-ray attenuation of the iodine-filled pediatric bladder 14. The contrast ratio of contrast element 24 with respect to the base 18 plus support 20 plus cover 22 is approximately 50. This ratio mimics the contrast between the soft tissue 10 and iodine-filled bladder 14 of the pediatric VCUG patient. One could apply the same principles in another embodiment if one wished to mimic the ratio of X-ray attenuation of the bladder 14 and the soft tissues 10 of an adult patient.

The first contrast element 24 could contain any material that mimics the X-ray attenuation of a patient's iodine-filled bladder. However, there are advantages in using an iodine-containing compound to mimic the iodine-containing liquid in the patient's bladder rather than, for example, a metal foil. These advantages go towards the problem of two materials which provide the same X-ray transmission when subjected to X-rays of a certain energy spectrum (measured as kVp), but have differing X-ray transmissions when subjected to X-rays of a different energy spectrum. If the first contrast element contains iodine, change in X-ray transmission of the phantom with variation in the X-ray energy spectrum will closely parallel the change in X-ray transmission of the clinical imaging situation.

Iodine and tin, which is the element closest to iodine in atomic number that is commonly available as a metal foil, are examples of materials which can provide the same X-ray transmission at a certain energy spectrum but yield differing X-ray transmissions at another energy spectrum. When 1.984 mm of potassium iodide, 1.068 mm of iodine and 0.584 mm of tin are separately subjected to an X-ray spectrum of 55 kVp, an identical X-ray transmission (mR/mAs) is measured. When the three materials are subjected to an X-ray spectrum of 60 kVp, tin transmits 46% more X-radiation than iodine, while potassium iodide transmits only 6.5% more. Therefore, the advantage of using iodine in the first contrast element 24 is especially important if one wishes to evaluate the performance of an imaging system or determine the X-ray dose to the phantom for more than one X-ray spectrum.

Referring again to FIG. 2 and 3, in the preferred embodiment the first contrast element 24 is a solid. In other embodiments, the first contrast element 24 could contain a liquid. The solid form is preferable because a liquid might leak or change with temperature shifts during storage.

Referring to FIG. 2, the first contrast element 24 is positioned in the center of the phantom. This positioning mimics the positioning of the patient's bladder 14 in the X-ray field during posterior-anterior projections of a VCUG exam. It is a particular imaging problem in VCUG exams that the patient's iodine-filled bladder is at the center of the viewing screen because in some X-ray examination mechanisms, the image acquisition system depends on sensing the radiation transmitted in the central portion of the image during the exam. Positioning the iodine-filled bladder in the center of the X-ray viewing screen puts the high X-ray attenuation element in the very center of the sense window of the automatic exposure control system. Because the iodine-containing bladder transmits very little X-radiation, the image in that region is dark and the automatic exposure control reacts by causing an over exposure of the portion of the image surrounding the bladder. This overexposure results in a loss of diagnostic information in that region. By employing the X-ray phantom of the present invention to calibrate the image acquisition system, the X-ray technician can avoid this over-exposure.

In the preferred embodiment, a second contrast element 26 is disposed within the base 18. This element 26 mimics a pediatric patient's pelvic bones 12 and has a contrast ratio of approximately 1.5 with respect to the base 18 plus support 20 plus cover 22. These same principles could be applied in another embodiment if one wished to mimic the attenuation value of adult pelvic bones.

Referring to FIG. 2, the second contrast element 26 is divided into two parts 26A and 26B. These plates 26 appear at the border of the X-ray field 16 when the phantom is correctly positioned between the X-ray emission and X-ray detection mechanisms. A suitable material for use in plates 26 is 1100 alloy aluminum with a thickness of 4-5 mm. The plates 26 may be attached to base 18 by various means. In the preferred embodiment, each plate 26 is attached with two threaded screws 34 which extend downward into threaded openings in the base 18.

Figure 4:
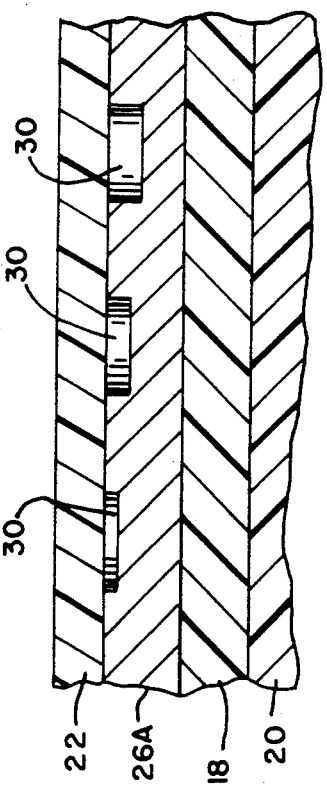
FIG. 4 is a cross-sectional view taken through line 4—4 in FIG. 2.

Referring to FIGS. 2 and 4, plate 26A contains a series of nine holes 30. These holes 30 are grouped into three size classes. As FIG. 4 illustrates, the holes of each size class vary in depth. In this manner, nine different combinations of hole size and depth are achieved. The holes 30 provide a series of low contrast test objects. Low contrast test objects allow an X-ray technician to calibrate the image acquisition system such that even objects with small X-ray attenuation differences might be seen.

Figure 5:
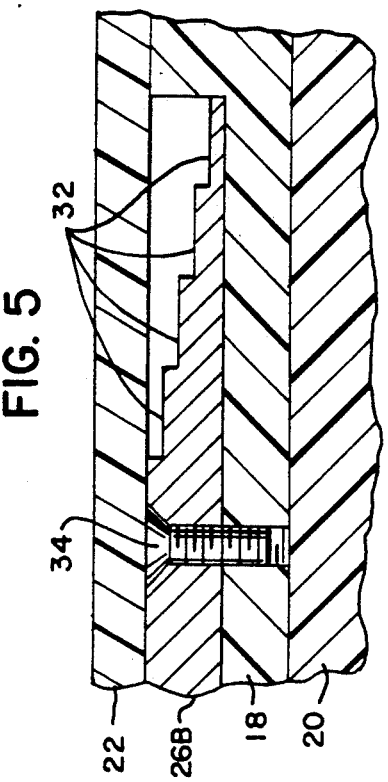
FIG. 5 is a cross-sectional view taken through line 5—5 in FIG. 2.

Referring to FIGS. 2 and 5, plate 26B has a series of incremental thickness steps 32 disposed along each of its ends. Preferably, each step is an increment of 1.0 mm of aluminum thickness and changes the image contrast by approximately 16%. These steps 32 provide a "gray scale" for the X-ray technician. A gray scale allows the technician to adjust the image acquisition system by imaging an object with known contrast differences.

Many modifications and variations of the preferred embodiment are possible without deviating from the spirit and scope of the invention. For example, other materials can mimic the X-ray attenuation needed for the various contrast elements. Additionally, placement of the contrast elements can vary somewhat and still provide the X-ray technician with sufficient contrast to calibrate the X-ray machine.

We claim:

1. A phantom for simulating a patient during an X-ray exam that involves introducing a high contrast substance into the patient, the combination comprising:
   a base composed of a first substance having a first X-ray attenuation; and
   a first contrast element composed of a second substance having a second X-ray attenuation, wherein the first contrast element is disposed within the base and the contrast ratio of the first contrast element to the base is approximately 50; and wherein the first contrast element has a shape that mimics a human bladder filled with a high contrast substance.

2. The phantom of claim 1, wherein the first contrast element contains iodine.

3. The phantom of claim 1, wherein the base has a shape which occupies the entire field of view of the X-ray exam and the first contrast element is positioned substantially in the center of the field of view.

4. The phantom of claim 4, wherein the first contrast element has a circular shape.

5. The phantom of claim 1, additionally comprising:
a second contrast element disposed within the base and having a third X-ray attenuation; wherein the contrast ratio of the second contrast element to the base is approximately 1.5.

6. The phantom of claim 5, wherein the first contrast element contains iodine.

7. The phantom of claim 5, wherein the first contrast element is in the center of the phantom.

8. The phantom of claim 7, wherein the first contrast element has a circular shape.

9. A phantom for use simulating a pediatric VCUG patient, the combination comprising:

a base composed of a first substance having a first X-ray attenuation;

a first contrast element composed of a second substance having a second X-ray attenuation, the first contrast element being disposed within the base and having a shape that mimics a child's bladder when filled with fluid, and wherein the contrast ratio of the first contrast element to the base is approximately 50; and wherein the first contrast element has a shape that mimics a pediatric bladder filled with a high contrast substance.

10. The phantom of claim 9, wherein the first contrast element contains iodine.

11. The phantom of claim 9, wherein the first contrast element is positioned on the base such that it appears in the center of an X-ray image when the phantom is properly positioned in the X-ray machine.

* * * * *